US 8,478,535 B2

(12) United States Patent
Jojic et al.

(10) Patent No.: US 8,478,535 B2
(45) Date of Patent: Jul. 2, 2013

(54) SYSTEMS AND METHODS THAT UTILIZE MACHINE LEARNING ALGORITHMS TO FACILITATE ASSEMBLY OF AIDS VACCINE COCKTAILS

(75) Inventors: Nebojsa Jojic, Redmond, WA (US); Vladimir Jojic, Redmond, WA (US); David E. Heckerman, Bellevue, WA (US); Brendan John Frey, Mississauga (CA); Christopher A. Meek, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 1639 days.

(21) Appl. No.: 11/324,506

(22) Filed: Dec. 30, 2005

(65) Prior Publication Data

US 2006/0178861 A1    Aug. 10, 2006

Related U.S. Application Data

(63) Continuation-in-part of application No. 10/977,415, filed on Oct. 29, 2004, now abandoned.

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 4,051,728 A | 10/1977 | Metz | |
| 4,235,871 A | 11/1980 | Papahadjopoulos et al. | |
| 4,342,566 A | 8/1982 | Theofilopoulos et al. | |
| 4,493,795 A | 1/1985 | Nestor, Jr. et al. | |
| 4,671,958 A | 6/1987 | Rodwell et al. | |
| 4,900,811 A | 2/1990 | Sutcliffe | |
| 5,019,369 A | 5/1991 | Presant et al. | |
| 5,426,039 A | 6/1995 | Wallace et al. | |
| 5,698,767 A | 12/1997 | Wilson et al. | |
| 5,709,843 A | 1/1998 | Reisner | |
| 2002/0182222 A1* | 12/2002 | Groot | 424/188.1 |
| 2004/0072249 A1 | 4/2004 | Hoffman et al. | |

OTHER PUBLICATIONS

Brejova et al., Finding Patterns in Biological Sequences, Technical report University of Waterloo, p. 1-49, Dec. 2000.*
Mourik et al., Determination of interaction potentials of amino acids from native protein structures: Tests on simple lattice models, Journal of Chemical Physics, vol. 110, Numb. 20, May 1999, pp. 10123-10133.*
Holley et al., Prediction of optimal peptide mixtures to induce broadly neutralizing antibodies to human immunodeficiency virus type 1, PNAS, vol. 88, p. 6800-6804, Aug. 1991.*
De Groot, Vaccine, vol. 19, p. 4385-4395, 2001.*
VanderVeen, WABI 2001, LNCS, vol. 2149, p. 264-277, 2001.*
Bailey et al., Unsupervised Learning of Multiple Motifs in Biopolymers Using Expectation Maximization, 1995, Machine Learning, 21, pp. 51-80.*
Shang et al. (Log-likelihood adaptive algorithm in single-layer perception based channel equalization, Electronics Letters, Oct. 26, 1995, vol. 31, No. 22, pp. 1900-1902).*
Southwood et al., Several Common HLA-DR Types Share Largely Overlapping Peptide Binding Repertoires, The Journal of Immunology, p. 3363-3373, Apr. 1998.*
Bailey, et al., "Unsupervised Learning of Multiple Motifs in Biopolymers Using Expectation Maximization", Machine Learning, vol. 21, pp. 51-80, 1995.
Blankenbecler, et al., "Matching Protein Structures with Fuzzy Alignments", PNAS, vol. 100 No. 21, pp. 11936-11940, Oct. 12, 2003.
Brejova, et al., "Finding Patterns in Biological Sequences", Technical Report University of Waterloo, pp. 1-49, Dec. 2000.
De Groot, et al., "From Genome to Vaccine: In Silico Predictions, Ex Vivo Verification", Vaccine, vol. 19, pp. 4385-4395, 2001.
Hernandez, et al., "Chimeric Synthetic Peptide as Antigen for Immunodiagnosis of HIV-1 Infection", Biochemical and Biophysical Research Communications, vol. 272, pp. 259-262, 2000.
Regenmortel, "Molecular Design Versus Empirical Discovery in Peptide-Based Vaccines. Coming to Terms with Fuzzy Recognitio Sites and III-Defined Structure-Function Relationship in Immunology", Vaccine, vol. 18, pp. 216-221, 2000.
Shang, et la. "Log-likelihood Adaptive Alogrithm in Single-layer Perception Based Channel Equalisation", Electronics Letters vol. 31, No. 22, pp. 1900-1902, Oct. 1995.
Van der Veen, et la., "Determinating of Binding Amino Acids Based on Random Peptide Array Screening Data" WABI 2001, LNCS, vol. 2149, pp. 264-277, 2001.
"Q&A: Microsoft Researchers Use Machine Learning Techniques to Help Advance HIV Vaccine Research" http://www.microsoft.com/presspass/features/2005/feb05/02-23HIVResearch.mspx. 5 pgs. Last Accessed: Sep. 15, 2006.
"Microsoft Research Collaborates With HIV Researchers to Create Advanced Vaccine Models Fact Sheet" http://www.microsoft.com/presspass/press/2005/feb05/0223HIVVaccineFS.mspx. 3 pgs. Last Accessed: Sep. 15, 2006.
"Microsoft Scientists Search for Breakthroughs in HIV Vaccine Design" http://www.microsoft.com/presspass/press/2005/feb05/02-23HIVVaccinePR.mspx. 3 pgs. Last Accessed: Sep. 15, 2006.

(Continued)

*Primary Examiner* — Jason Sims
(74) *Attorney, Agent, or Firm* — Lee & Hayes, PLLC

(57) ABSTRACT

The subject invention provides systems and methods that facilitate AIDS vaccine cocktail assembly via machine learning algorithms such as a cost function, a greedy algorithm, an expectation-maximization (EM) algorithm, etc. Such assembly can be utilized to generate vaccine cocktails for species of pathogens that evolve quickly under immune pressure of the host. For example, the systems and methods of the subject invention can be utilized to facilitate design of T cell vaccines for pathogens such HIV. In addition, the systems and methods of the subject invention can be utilized in connection with other applications, such as, for example, sequence alignment, motif discovery, classification, and recombination hot spot detection. The novel techniques described herein can provide for improvements over traditional approaches to designing vaccines by constructing vaccine cocktails with higher epitope coverage, for example, in comparison with cocktails of consensi, tree nodes and random strains from data.

47 Claims, 8 Drawing Sheets

OTHER PUBLICATIONS

Figure 1:
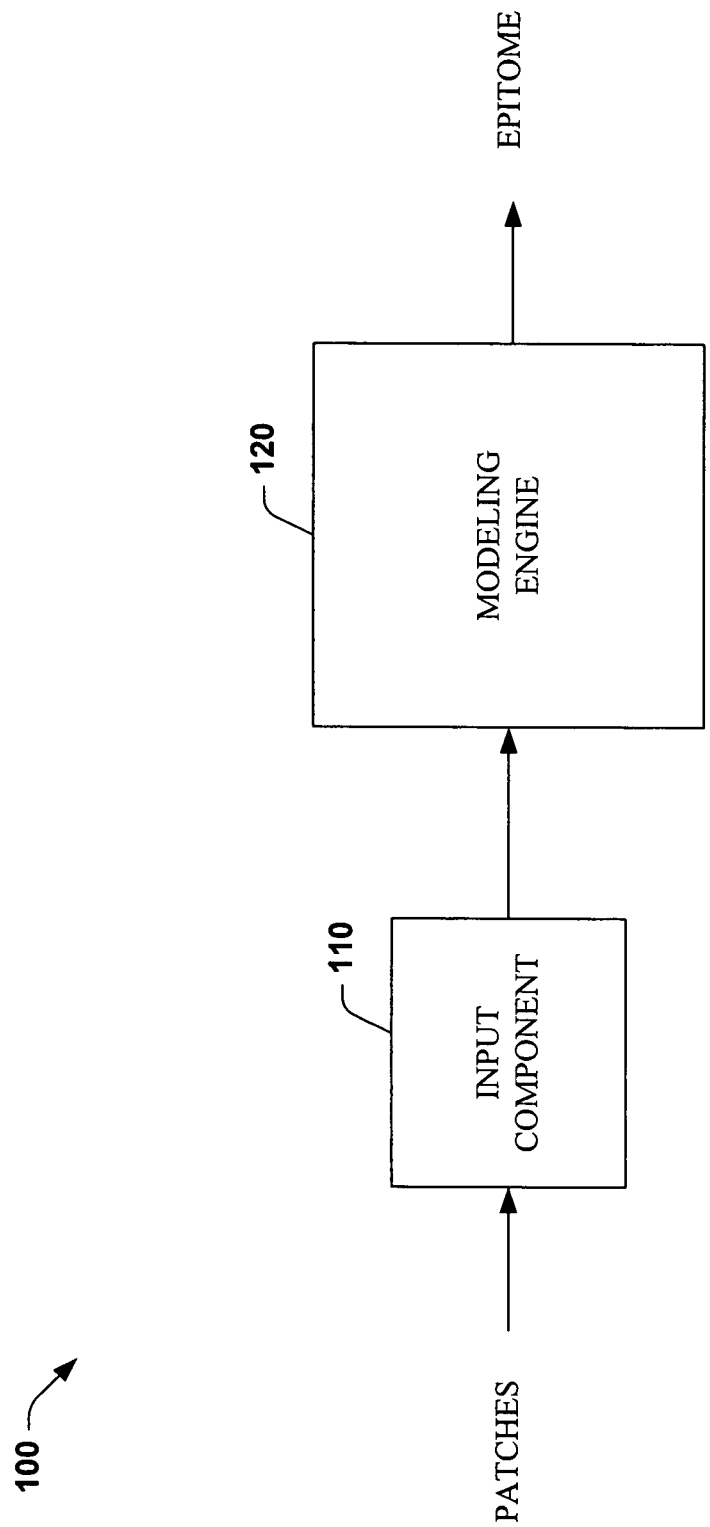

Moore et al. "Evidence of HIV-1 Adaptation to HLA-Restricted Immune Responses at a Population Level." Science, vol. 296, Issue 5572, pp. 1439-1443, May 24, 2002.

McKinney et al. "Recognition of Variant HIV-1 Epitopes from Diverse Viral Subtypes by Vaccine-Induced CTL1." The Journal of Immunology, 2004, pp. 1941-1950, vol. 173.

Jojic et al. "HLA-driven Optimization of an HIV Vaccine Immunogen." 12th Conference on Retroviruses and Infections, Feb. 22-25, 2005. 1 pg.

Jojic et al. "HLA-driven Optimization of an HIV Vaccine Immunogen Using Epitomes." 30 pgs.

"CTLPred: A SVM & ANN Based CTL epitope Prediction method" http://www.imtech.res.in/raghava/ctlpred/about.html 7 pgs. Last Accessed: Sep. 15, 2006.

"HIV Databases" http://www.hiv.lanl.gov/content/index. Last Accessed: Feb. 13, 2007. 2 pgs.

"SYFPEITHI" http://www.SYFPEITHI.de. Last Accessed: Sep. 15, 2006. 1 pg.

Kohavi. "A study of cross-validation and bootstrap for accuracy estimation and model selection." In Proceedings of the Fourteenth International Joint Conference on Artificial Intelligence, pp. 1137-1143. San Mateo, CA: Morgan Kaufmann, 1995. 7 pgs.

Cheeseman, et al., "Bayesian Classification(AutoClass):Theory and Results", in Advances In Knowledge Discovery and Data Mining, Fayyad, U., Piatesky-Shapiro, G., Smyth, P., and Uthurusamy, R., eds (AAAI Press, 1995), 23 pages.

Cheung, et al., "Video epitomes", CPVR, Jun. 2005, 8 pages.

Durbin et al., "Biological sequence analysis Probabilistic models of proteins and nucleic acids", Cambridge University Press, 1998, 366 pages.

Felsenstein, PHYLIP (Phylogeny Inference Package) version 3.6, Jan. 2004, 68 pages.

Jojic, et al., "Epitomic analysis of appearance and shape", In Proceedings of the Ninth International Conference on Computer Vision, 2003, 8 pages.

Kapoor et al., "The Audio Epitome: A New Representation for Modeling and Classifying Auditory Phenomena", JCASSP, 2004, 4 pages.

Neal, et al., "A view of the EM algorithm that justifies incremental, sparse, and other variants", in MIT Press, 1999, 14 pages.

Office Action for U.S. Appl. No. 11/324,467, mailed on Oct. 26, 2011, Simon Mallal, "Association-Based Epitope Design", 12 pgs.

Office Action for U.S. Appl. No. 11/324,691, mailed on Mar. 26, 2012, Nebojsa Jojic, "Systems and Methods That Utilize Machine Learning Algorithms to Facilitate Assembly of Aids Vaccine Cocktails", 15 pgs.

Allen, et al., "Selection, Transmission, and Reversion of an Antigen-Processing Cytotoxic T-Lymphocyte Escape Mutation in Human Immunodeficiency Virus Type 1 Infection." Journal of Virology, Jul. 2004, pp. 7069-7078, vol. 78, No. 13. 10 pgs.

Leslie, et al., "Transmission and accumulation of CTL escape variants drive negative associations between HIV polymorphisms and HLA." JEM, Mar. 21, 2005. pp. 891-902, vol. 201, No. 6. 12 pgs.

Leslie et al., "HIV evolution: CTL escape mutation and reversion after transmission." Nat Med 10(3):282-289, 2004. 25 pgs.

Parker et al. "Scheme for ranking potential HLA-A2 binding peptides based on independent binding of individual peptide side-chains." Journal of Immunology. 1994. 152:163-75. 13 pgs.

Jojic et al. "Using 'epitomes' to model genetic diversity: Rational design of HIV vaccine cocktails." Presented at the Conference on Neural Information Processing Systems on Dec. 7, 2005. 7 pgs.

Bhasin et al. "MHCBN: A comprehensive database of MHC binding and non binding peptides," Bioinformatics (2003) vol. 19. 665-666. 2 pgs.

Rammensee et al. "SYFPEITHI: database for MHC ligands and peptide motifs," Immmunogenetics (1999) 50:213-219. 7 pgs.

Nolan et al. "Impact of host genetics on HIV disease progression and treatment: new conflicts on an ancient battle ground." AIDS: vol. 18(9). Jun. 18, 2004. pp. 1231-1240. 14 pgs.

Feeney et al. "HIV-1 viral escape in infancy followed by emergence of a variant-specific CTL response." Journal of Immunology. Jun. 15, 2005; 174(12). pp. 7524-7529. 7 pgs.

Mallal. "HIV adaptation to genetic polymorphisms of the host." 10th Conference on Retroviruses and Opportunistic Infections. Boston, MA, Feb. 10-14, 2003. 1 pg.

Mallal et al. "HIV adaptation to HLA-restricted immune responses—implications for vaccine design and evaluation." 10th Conference on Retroviruses and Opportunistic Infection, Boston, MA. Feb. 10-14, 2003. Abstract No. C-27 (327). 1 pg.

Allen et al. "Stereotypic escape from CD8+ T cell responses represents a major driving force of HIV-1 sequence diversity and reveals constraints on HIV-1 evolution." 12th Conference on Retroviruses and Opportunistic Infections, Boston, MA, Feb. 22-25, 2005. Abstract No. 463. 1 pg.

Park et al. "HLA-restricted immune responses have driven the evolution of HIV-1 clades." 12th Conference on Retroviruses and Opportunistic Infections, Boston, MA, Feb. 22-25, 2005. 2 pgs.

Jojic et al., HLA-driven optimization of an HIV vaccine immunogen. 12th Conference on Retroviruses and Opportunistic Infections, Boston USA, Feb. 22-25, 2005. Session 89 Poster Abstracts. 2 pgs.

"Q&A: Microsoft Researchers Use Machine Learning Techniques to Help Advance HIV Vaccine Research." http://www.microsoft.com/presspass/features/2005/feb05/02-23HIVResearch.mspx. Last accessed on Feb. 13, 2007. 5 pgs.

"Microsoft Research Collaborates With HIV Researchers to Create Advanced Vaccine Models Fact Sheet." http://www.microsoft.com/presspass/press/2005/feb05/0223HIVVaccineFS.mspx. Last accessed on Sep. 25, 2006. 3 pgs.

Bhasin et al. "Prediction of CTL epitopes using QM, SVM and ANN techniques." http://www.ncbi.nlm.nih.gov/entrez/query.fcgi?CMD=Display&DB=pubmed. Last accessed on Sep. 25, 2006. 2 pgs.

Jin et al. "Identification of Subdominant Cytotoxic T Lymphocyte Epitopes Encoded by Autologous HIV Type 1 Sequences, Using Dendritic Cell Stimulation and Computer-Driven Algorithm." AIDS Research and Human Retroviruses. vol. 16, No. 1, 2000, pp. 67-76. 10 pgs.

Bird et al. "HLA typing in a Kenyan cohort identifies novel class I alleles that restrict cytotoxic T-cell responses to local HIV-1 clades." AIDS. 2002. vol. 16. pp. 1899-1904. 6 pgs.

Fang et al. "Analysis of Transition from Long-Term Nonprogressive to Progressive Infection Identifies Sequences that May Attenuate HIV Type 1." Aids Research and Human Retroviruses. vol. 17, No. 15, 2001, pp. 1395-1404. 10 pgs.

Yuste et al. "Unusual Distribution of Mutations Associated with Serial Bottleneck Passages of Human Immunodeficiency Virus Type 1." Journal of Virology. vol. 74, No. 20. Oct. 2000, p. 9546-9552. 7 pgs.

Anderson et al. "Nef from Primary Isolates of Human Immunodeficiency Virus Type 1 Suppresses Surface CD4 Expression in Human and Mouse T Cells." Journal of Virology. Aug. 1993, vol. 67, No. 8. p. 4923-4931. 9 pgs.

Gunthard et al. "Human Immunodeficiency Virus Replication and Genotypic Resistance in Blood and Lymph Nodes after a Year of Potent Antiretroviral Therapy." Journal of Virology. Mar. 1998, p. 2422-2428. vol. 72, No. 3. 7 pgs.

Desire et al. "Quantification of Human Immunodeficiency Virus Type 1 Proviral Load by a TaqMan Real-Time PCR Assay." Journal of Clinical Microbiology. Apr. 2001, vol. 39, No. 4. p. 1303-1310. 8 pgs.

Connor et al. "Immunological and Virological Analyses of Persons Infected by Human Immunodeficiency Virus Type 1 while Participating in Trials of Recombinant gp120 Subunit Vaccines." Journal of Virology. vol. 72, No. 2. Feb. 1998, pp. 1552-1576.

Peters et al. "Resistance to Nucleoside Analog Reverse Transcriptase Inhibitors Mediated by Human Immunodeficiency Virus Type 1 p6 Protein." Journal of Virology. vol. 75, No. 20. Oct. 2001, pp. 9644-9653. 10 pgs.

Carr et al. "Diverse BF recombinants have spread widely since the Introduction of HIV-1 into South America." AIDS 2001, vol. 15 No. 15. p. 41-47. 7 pgs.

MacRiota et al, "Detection of Simian Immunodeficiency Virus in Diverse Species and of Human Immunodeficiency Virus Type 2 by Using Consensus Primers within the pol Region." Journal of Clinical Microbiology. Sep. 2002, vol. 40, No. 9. 5 pgs.

Holguin et al. "Prevalence of Human Immunodeficiency Virus Type 1 (HIV-1) Non-B Subtypes in Foreigners Living in Madrid, Spain, and Comparison of the Performances of the Amplicor HIV-1 Monitor Version 1.0 and the New Automated Version 1.5." Journal of Clinical Microbiology. May 2001, p. 1850-1854. vol. 39, No. 5. 5 pgs.

Schueler-Furman et al. "Structure-based prediction of binding peptides to MHC class I molecules: Application to a broad range of MHC alleles." Protein Science. 2000. vol. 9. pp. 1838-1846. 9 pgs.

"Microsoft Scientists Search for Breakthroughs in HIV Vaccine Design." http://www.microsoft.com/presspass/press/2005/feb05/02-23HIVVaccinePR.mspx. Last accessed on Sep. 25, 2006. 3 pgs.

* cited by examiner

```
                              SEQUENCE LISTING

<160> NUMBER OF SEQ ID NOS: 13

<210> SEQ ID NO 1
<211> LENGTH: 50
<212> TYPE: PRT
<213> ORGANISM: Artificial Sequence
<220> FEATURE:
<223> OTHER INFORMATION: Synthetic example used for illustration
      purposes

<400> SEQUENCE: 1

Met Leu Ile Cys Lys Arg Asp Cys Ile Ala Glu Leu Asp Arg Gln Lys
1               5                   10                  15

Lys Met Met Asn Ile His Glu Cys Ile Thr Ala Phe Trp Phe Ser Lys
            20                  25                  30

Asp Pro Val Glu Pro Asp Pro Thr Trp Lys Gly Trp Met Thr Glu
        35                  40                  45

His Gln
    50

<210> SEQ ID NO 2
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 2

Leu Ile Cys Lys Arg Asp Cys Ile Ala Glu Leu Asp Met Asn Ile His
1               5                   10                  15

Glu Cys Ile Thr Ala Phe Pro Asp Pro Thr Trp Lys Gly Trp Trp Met
            20                  25                  30

Thr Glu His Gln Ala Met Met Gln Trp
        35                  40

<210> SEQ ID NO 3
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 3

Ala Phe Leu Ser Lys Phe Gly Tyr Tyr Cys Asn Ile His Glu Cys Ile
1               5                   10                  15

Thr Ala Phe Trp Phe Ser Asn Glu Asn Glu Leu Lys Asp Pro Val Glu
            20                  25                  30

Pro Asp Pro Thr Trp Lys Gly Trp Glu
        35                  40

<210> SEQ ID NO 4
<211> LENGTH: 43
<212> TYPE: PRT
<213> ORGANISM: Artificial Sequence
```

```
<220> FEATURE:
<223> OTHER INFORMATION: Synthetic example used for illustration
      purposes

<400> SEQUENCE: 4

Cys Lys Arg Asp Cys Ile Ala Glu Leu Asp Arg Gln Lys Ile His Glu
1               5                   10                  15

Cys Ile Thr Ala Phe Trp Phe Val Glu Pro Asp Pro Thr Trp Lys Gly
            20                  25                  30

Trp Trp Met Thr Thr Glu His Gln Trp Met Thr
            35                  40

<210> SEQ ID NO 5
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 5

Glu Asn Arg Glu Ala Lys Lys Met Met Asn Ile His Glu Cys Ile Thr
1               5                   10                  15

Ala Phe Cys Phe Ser Lys Asp Pro Val Glu Pro Asp Pro Thr Trp Lys
            20                  25                  30

Gly Ser His Gly Trp Trp Met Thr Glu
            35                  40

<210> SEQ ID NO 6
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 6

Met Val Asn Asn Glu Asp Glu Val Glu Thr Asn Ile Trp Ser Lys Lys
1               5                   10                  15

Met Met Asn Ile His Glu Cys Ile Thr Ala Phe Cys Arg Phe Ser Lys
            20                  25                  30

Asp Pro Val Glu Pro Asp Pro Thr Trp
            35                  40

<210> SEQ ID NO 7
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 7

Met Thr Met His Asp Cys Ile Ala Glu Leu Asp Arg Gln Lys Lys Met
1               5                   10                  15

Met Ile Asp Arg Cys Ile Thr Ala Phe Trp Phe Ser Lys Asp Pro His
            20                  25                  30

Val Glu Pro Asp Pro Thr Trp Lys Gly
            35                  40

<210> SEQ ID NO 8
<211> LENGTH: 42
<212> TYPE: PRT
<213> ORGANISM: Artificial Sequence
```

```
<220> FEATURE:
<223> OTHER INFORMATION: Synthetic example used for illustration
      purposes

<400> SEQUENCE: 8

Phe Arg Gln Tyr Ser Cys Lys Lys Arg Asp Cys Ile Ala Glu Leu Asp
1               5                   10                  15

Arg Gln Lys Lys Met Met Ala Met Asn Ile His Glu Cys Ile Thr Ala
            20                  25                  30

Phe Trp Phe Ser Lys Asp Phe Ile Leu Ala
        35                  40

<210> SEQ ID NO 9
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 9

Cys Glu Ile Ala Glu Leu Asp Arg Gln Lys Lys Met Met Asn Gln Trp
1               5                   10                  15

Phe Ser Lys Asp Pro Val Glu Pro Asp Pro Thr Ala Lys Gly Trp Trp
            20                  25                  30

Met Thr Glu His Gln His Gln Thr Ile
        35                  40

<210> SEQ ID NO 10
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 10

Asn Ile Asn Met Phe Trp Phe Ser Lys Asp Pro Val Glu Pro Asp Pro
1               5                   10                  15

Thr Trp Asp Gln His Gly Pro Leu Met Lys Gly Trp Trp Met Thr Glu
            20                  25                  30

His Gln Thr Thr Glu His Gln Glu His Gln
        35                  40

<210> SEQ ID NO 11
<211> LENGTH: 43
<212> TYPE: PRT
<213> ORGANISM: Artificial Sequence
<220> FEATURE:
<223> OTHER INFORMATION: Synthetic example used for illustration
      purposes

<400> SEQUENCE: 11

Cys Lys Arg Asp Cys Ile Ala Glu Leu Asp Arg Gln Lys Lys Glu Glu
1               5                   10                  15

Val Ile Pro Asn Ile His Glu Cys Ile Thr Ala Phe Trp Phe Ser Lys
            20                  25                  30

Asp Pro Val Val Glu Pro Asp Pro Thr Trp Lys
        35                  40

<210> SEQ ID NO 12
<211> LENGTH: 41
<212> TYPE: PRT
<213> ORGANISM: Artificial Sequence
```

-continued

```
<220> FEATURE:
<223> OTHER INFORMATION: Synthetic example used for illustration
      purposes

<400> SEQUENCE: 12

Gln Lys Lys Met Met Asn Ile His Glu Cys Ile Thr Ala Trp Phe Ser
1               5                   10                  15

Lys Asp Pro Val Glu Pro Asp Pro Thr Trp Gly Trp Trp Met Thr Glu
                20              25                  30

His Gln Gln Ile Arg Phe Ala Ile Gln
                35              40

<210> SEQ ID NO 13
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 13

Lys Arg Asp Cys Ile Ala Glu Leu Asp Arg Gln Lys Lys Met Met Ala
1               5                   10                  15

Phe Trp Phe Ser Lys Asp Pro Val Glu Pro Asp Pro Thr Leu Phe Ile
                20              25                  30

Trp Lys Gly Trp Trp Met Thr Glu His Gln
                35              40
```

SYSTEMS AND METHODS THAT UTILIZE MACHINE LEARNING ALGORITHMS TO FACILITATE ASSEMBLY OF AIDS VACCINE COCKTAILS

CROSS-REFERENCE TO RELATED APPLICATIONS

This application is a Continuation-in Part of U.S. patent application Ser. No. 10/977,415, entitled "SYSTEMS AND METHODS THAT UTILIZE MACHINE LEARNING ALGORITHMS TO FACILITATE ASSEMBLY OF AIDS VACCINE COCKTAILS," filed Oct. 29, 2004 now abandoned. This application is also related to U.S. patent application Ser. No. 11/324,506, entitled, "SYSTEMS AND METHODS THAT UTILIZE MACHINE LEARNING ALGORITHMS TO FACILITATE ASSEMBLY OF AIDS VACCINE COCKTAILS", filed Dec. 30, 2005. The entireties of the aforementioned applications are incorporated herein by reference.

BACKGROUND

The human body has the ability to develop extremely powerful specific immunity against individual invading agents such as lethal bacteria, viruses, toxins, etc. This ability is typically referred to as acquired immunity. In general, two basic but closely allied types of acquired immunity occur in the body. In one type, the body develops circulating antibodies (referred to as bursal, or B lymphocytes), which are globulin molecules that are capable of attacking an invading agent. This type of acquired immunity is referred to as humoral immunity. The other type of acquired immunity is achieved through the formation of large numbers of activated lymphocytes (referred to as thymic, or T lymphocytes or T cells) that are specifically designed to destroy a foreign agent. This type of immunity is called cell-mediated immunity.

Upon exposure to particular antigens, T lymphocytes of the lymphoid tissue proliferate and release large numbers of activated T cells. These T cells pass into the circulation and are distributed throughout the body, passing through the capillary walls into the tissue spaces, back into the lymph and blood once again, and circulating again and again throughout the body, sometimes lasting for month or even years. In addition, T lymphocyte memory cells are formed and preserved in the lymphoid tissue and become additional T lymphocytes of that specific clone. These additional T lymphocytes can spread throughout the lymphoid tissue of the body, and, on subsequent exposure to the same antigen, the release of activated T cells can occur far more rapidly and much more powerfully than in a first response.

Cytotoxic T cells are direct attack cells that are capable of killing microorganisms and the body's own cells and, thus, are often referred to as "killer" cells. In general, the receptor proteins on the surfaces of the cytotoxic cells cause them to bind tightly to those organisms or cells that contain their binding-specific antigen. In the instance of the Human Immunodeficiency Virus (HIV), the immune system of the infected human produces killer T-cells that recognize epitopes (patterns of 8-11 amino acids) on the surface of T cells infected by HIV and bind thereto. The immediate affect of the binding is swelling of the T cell and release of cytotoxic substances into the attacked cell with eventual destruction of the cell. Cytotoxic T cells are especially lethal to tissue cells that have been invaded by viruses since many virus particles become entrapped in the membranes of these cells and attract the T cells due to viral antigenicity.

Through exposure to pathogen or pathogen-like proteins, the adaptive immune system can be primed to react to as many foreign amino acid patterns as possible, given resource and specificity constraints. Such exposure can be achieved through vaccines, which have been used for many years to cause acquired immunity against specific diseases.

Pathogen evolution typically converges to a balance between avoiding detection and preserving functionality. As the immune system has a localized effect on the pathogen's genome, the evolution will be different in different hosts and different in different parts of the pathogen's proteins. With traditional approaches to designing vaccines for rapidly evolving pathogens, evolution typically is modeled as a process of random site-independent mutations, wherein total mutation in a genome or an entire protein is assumed to capture evolutionary distance between a pair of sequences. However, the environment can affect disparate pieces of the genome and/or peptides in a protein differently. On the population level, this can lead to creation of several functional versions of each piece that are essentially arbitrarily combined into a whole protein. The combinatorial growth of functional forms of the protein creates an impression of immense diversity when mutation is averaged over the genome. Another deficiency with traditional approaches is the log mutation scores for sites in a sequence are summed together (or mutation probabilities are all multiplied together) to define a number corresponding to an evolutionary distance between two sequences when separate pieces commonly have different evolutionary distances. Thus, there is a need for improved techniques that facilitate vaccine assembly.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The subject invention provides system and methods that facilitate vaccine cocktail assembly via machine learning techniques that model sequence diversity. Such assembly can be utilized to generate vaccine cocktails for species of pathogens that evolve quickly under immune pressure of the host. For example, the systems and methods of the subject invention can be utilized to facilitate design of T cell vaccines for pathogens such HIV. In addition, the systems and methods of the subject invention can be utilized with other applications, such as, for example, sequence alignment, motif discovery, classification, and recombination hot spot detection.

A resultant vaccine cocktail can be referred to as an "epitome," or a sequence that includes all or many of the short subsequences from a large set of sequence data, or population. The novel techniques described herein can provide for improvements over traditional approaches that utilize an ancestral sequence from which diversity mushroomed, an average sequence of a population, or a "best" sequence a population. For example, vaccine cocktails generated by the systems and methods of the subject invention can provide for higher epitope coverage in comparison with the cocktails of consensi, phylogenetic tree nodes and random strains from the data. In addition, consensus models and/or phylogenetic tree models are not well-suited to accounting for the large amount of local diversity in HIV.

In one aspect, a system and/or method that determines epitomes for rapidly evolving pathogens is provided. The system can include an input component that receives a plurality of patches (e.g., sequences of DNA, RNA, or protein, etc.). Such patches can be a subset or all of a population of patches. The received patches can be variable length and conveyed by the input component to a modeling engine. The modeling engine can employ various learning algorithms (e.g., expectation-maximization (EM), greedy, Bayesian, Hidden Markov, etc.) to determine the epitome. For example, the modeling engine can determine a most likely epitome, such as, a sequence (e.g., with the greatest coverage and a shortest sequence for a particular coverage. Upon determining the epitome, it can be sequenced to create a peptide and/or nucleotide.

In another aspect of the subject invention, systems and methods are provided for designing AIDS/HIV vaccine cocktail. In one instance, the methods include obtaining AIDS sequence data of contiguous amino acid subsequences (e.g., all possible subsequences with length that corresponds to a typical epitope), building a plurality of disparate sized patches from the sequence data by iteratively increasing a size of a patch while decreasing an associated free energy (e.g., set equal to zero), aggregating patches to form the AIDS vaccine cocktail by adding a most frequent patch during each iteration unless the patch was already added. An expectation-maximization (EM) and/or a greedy algorithm can be utilized to optimize respective iterations. In another instance, the methods include receiving a plurality of HIV related sequences, utilizing the sequences, based on their linear nine-amino acid epitopes (e.g., substantially equally immunogenic), to create a compact representation of a large number of HIV related peptides, employing a machine learning algorithm to optimize the representation in terms of binding energies, and designing an HIV vaccine cocktail based on the representation. Alternatively, the representation can be estimated from the sequence by parsing the sequences into shorter peptides and creating a mosaic sequence that is longer than any individual sequence.

In yet another instance, the systems include a component that receives a plurality of HIV related nine-mers, a component that generates a sequence that epitomizes the plurality of nine-mers, a component that employs a greedy algorithm (e.g., initialized with a random nine-mer and a variable binding energy estimate) to jointly update a size of the sequence and a free energy, and a component that utilizes the updated sequence to design an HIV vaccine cocktail. Additionally or alternatively, an expectation-maximization algorithm that concurrently optimizes the updated sequence and a binding energy can be utilized.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

BRIEF DESCRIPTION OF THE DRAWINGS

FIG. 1 illustrates an exemplary system that employs machine learning to determine epitomes for rapidly evolving pathogens.

FIG. 2 illustrates an exemplary system that utilizes a cost function to facilitate determining epitomes.

FIG. 3 illustrates an exemplary system that utilizes an expectation-maximization (EM) algorithm to facilitate determining epitomes.

FIG. 4 illustrates an exemplary method for determining epitomes.

FIG. 5 illustrates an exemplary epitome.

FIG. 6 is a graph depicting gene coverage versus length.

FIG. 7 is a graph depicting epitope coverage versus length.

FIG. 8 illustrates an exemplary operating environment.

DETAILED DESCRIPTION

The subject invention relates to systems and methods that utilize machine learning to model sequence diversity to facilitate vaccine cocktail assembly. Suitable machine learning techniques include cost functions, expectation-maximization (EM) and greedy algorithms, for example. Such assembly can be utilized to generate vaccine cocktails for species of pathogens that evolve quickly under immune pressure of the host. For example, the systems and methods of the subject invention can be utilized to facilitate design of T cell vaccines for pathogens such HIV.

The present invention is described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As utilized herein, the terms "epitome," "sequence," "instance of a model," and the like generally refers to a sequence that includes all or many of the short subsequences (patches) from a large set or population of sequence data and/or a sequence whose subsequences (patches) can be assembled to generate a wide range of representative sequences of a desired category. Suitable categories include sequences associated with a specific species, such as HIV, sequences from a specific clade, and/or sequences associated with an acute or chronic phase of infection.

FIG. 1 illustrates a system 100 that determines epitomes (vaccine cocktails) for rapidly evolving pathogens such as HIV. The system 100 comprises an input component 110 and a modeling engine 120. The input component 110 can receive a plurality of patches that can be a subset or all of a population of patches, wherein such patches can be utilized to construct an epitome. The received patches can be variable length, for example, nine-mers, ten-mers, etc. The input component 110 can convey the patches to the modeling engine 120, which can employ various learning algorithms (e.g., expectation-maximization (EM), greedy, Bayesian, Hidden Markov, etc.) that can utilize the patches to determine the epitome. For example, the modeling engine 120 can be utilized to determine a most likely epitome. In one instance, the most likely epitome is defined as the sequence with the greatest coverage. In another instance, the most likely epitome is defined as the shortest sequence for a particular coverage. Upon determining the epitome, it can be utilized to create peptide and/or nucleotide sequencing.

Traditional approaches to designing such vaccines typically model evolution as a process of random site-independent mutations. However, the environment can affect different pieces of the genome and/or peptides in a single protein differently. On the population level, this can lead to creation of several functional versions of each piece and an impression of immense diversity. In addition, with traditional approaches the log mutation scores for sites in a sequence are summed together or mutation probabilities are multiplied together to define a number corresponding to an evolutionary distance between two sequences, when separate pieces commonly have different evolutionary distances. The novel approach employed by the system 100 can provide for improvements over traditional technique via utilizing machine learning techniques. By way of example, the system 100 can be employed to model sequence diversity to facilitate generating of vaccine cocktails. Such cocktails can provide for higher epitope coverage in comparison with the cocktails of consensi, phylogenetic tree nodes and random strains from the data.

Figure 2:
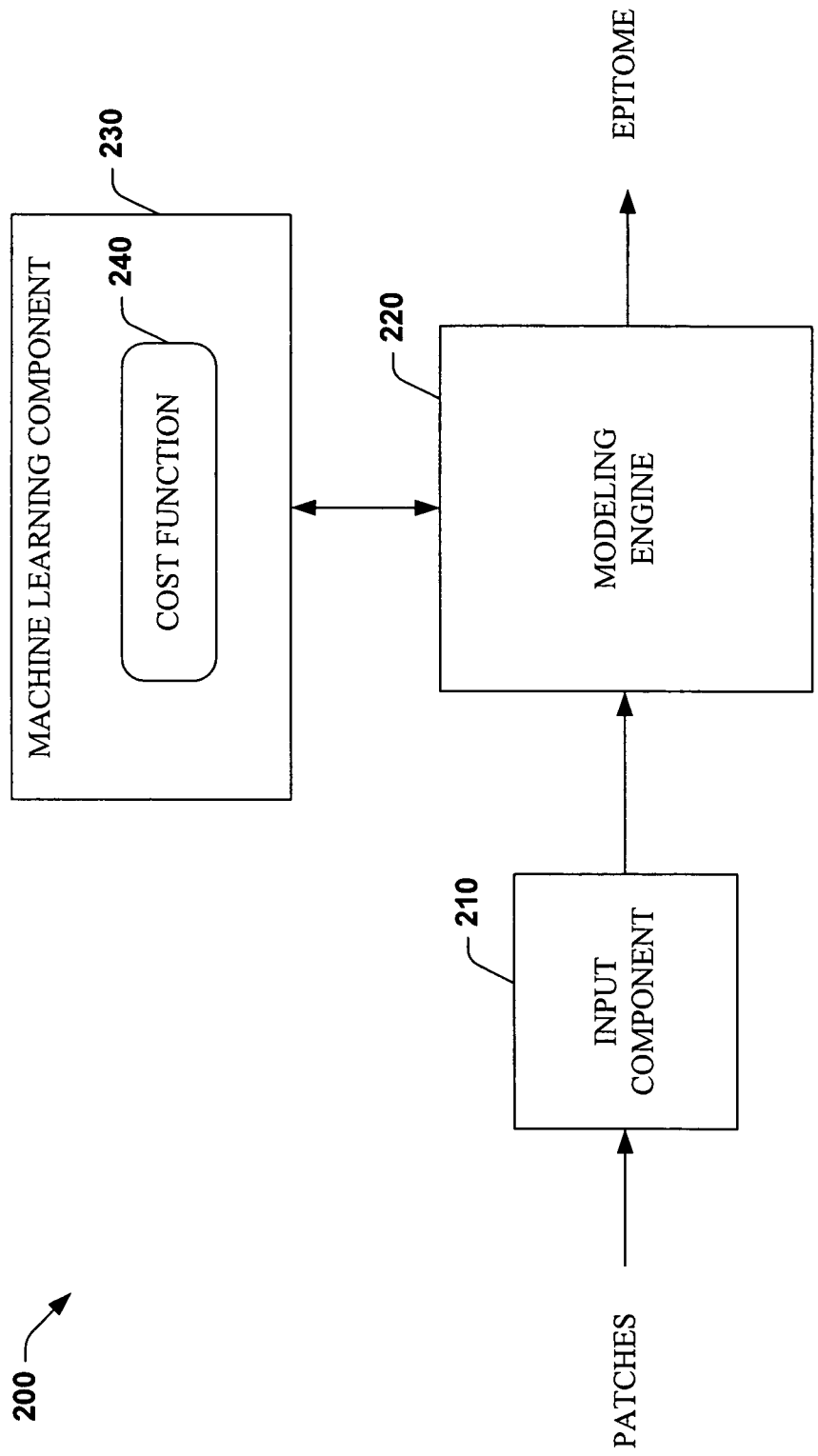

FIG. 2 illustrates a system 200 that determines epitomes via a cost function. The system 200 comprises an input component 210, a modeling engine 220, and a learning component 230. The input component 210 can receive patches associated with a population and convey the patches to the modeling engine 120, which can utilize the patches to determine the epitome. The modeling engine 220 can employ the learning component 230 to facilitate determining the epitome.

In one aspect of the subject invention, the learning component 230 can employ a cost function 240 to learn the epitome. For example, the learning component 230 can employ a cost function 240 that measures the similarity of sequence data with an estimate of the epitome. By way of example, a set of nucleotide or amino acid patches defined by $x=\{x_{ij}\}$, wherein $i=1,\ldots,M$ (M is a sequence index) and $j=1,\ldots,N$ (N is a site (position) index) can be received by the input component 210 and conveyed to the modeling engine 220. The modeling component 220 can utilize the patches to construct an M×N matrix/array of sequence data (an epitome) that can be input to a learning algorithm that renders the epitome as a smaller array $e=\{e_{mn}\}$ of size Me×Ne, wherein MeNe<<MN. For example, the data can include 12 sequences (M=12) with lengths of about 42 (N=42), whereas the epitome size after utilizing the learning algorithm can be reduced to Me=1 and Ne=50. It is to be appreciated that the values utilized in the above example are illustrative and do not limit the invention. Moreover, it is to be appreciated that the learning algorithm can optimize the epitome in order to maximize a number of short subsequences that are present in the input data, and the input data can be described by its epitome and a mapping that links the sites in the data to sites in the epitome.

In order to establish such mapping, the sequence set (patches) x can be represented as a set of short overlapping subsequences, wherein respective subsequence $x_S$ can include letters from a subset of sequence positions S. Each index in an index set S generally is two dimensional, pointing both to a sequence and a position within the sequence. These subsequences can be defined on arbitrary biological sequences. For example, if X contains M sequences of length N, then the total number of contiguous patches in the data of length n is M(N−n) and, thus, the cardinality of S is M(N−n). For each patch $x_S$, its index set S can be mapped to a hidden set of epitome indices T. In many instances contiguous patches $x_S$ can be assumed to map to contiguous patches $e_T$ in the epitome so the set T can be identified by the first index in the set. A number of possible mappings for each patch is defined by Me(Ne−n). For HIV amino acid sequence data, these subsequences generally are peptides that can correspond to epitopes. With T cell HIV vaccines, the patch length may be equal to the epitope length (e.g., 8-11 amino acids). However, the context in regions adjacent to the epitopes can affect HLA binding so the patch length may be longer, for example, up to about 33 amino acids.

The cost function employed by the learning component 230 to optimize the epitome depends on the application. For example, a cost function that accounts for various acts that are needed to mount an effective immune response can be utilized, wherein each act can have an associated cost in the form of an energy. This energy can be viewed as a negative log-probability of an event. By way of example, a cost function can be selected to account for the acts utilized to kill an infected cell, for example, the acts needed for a vaccine e to generate an effective immune response. The vaccine generally is chopped up by cellular mechanisms and short subsequences (e.g., epitopes) are presented on the surface of the processing cell. A positive immune response happens if the clone of the same T cell can later bind to a virus epitope $x_S$ that an infected cell presents on its surface, initiating the killing of the infected cell.

In a cell processing a vaccine e, a peptide can be presented on the surface and bound to a T cell in a process with priming energy E(T). The priming energy typically is the sum of the cleavage, HLA binding, transport and/or T cell binding energies, which can influence priming of an appropriate T cell to attack a cell that presents an epitope pattern similar to $e_T$. In addition, sequence data neighboring an epitope can have an impact on presentation and, thus, on the priming energy. A T cell primed with the vaccine epitope $e_T$ typically attacks a cell that presents a virus epitope $x_S$ in a process with attack energy $E(x_S, e_T)$. This energy depends on the cross-reactivity of the T cell. If the patch length is selected so as to account for each epitope plus its neighboring contextual sequence data, then only a piece of a window corresponding to the actual epitope can be utilized to determine the attack energy. The T cell attack energy is lowest when the epitope substantially matches the amino acid pattern on the T cell. The energy associated with priming with $e_T$ and attacking $x_S$ can be determined by summing the two energies E(T) and $E(x_S, e_T)$.

In general, for an effective immune response the energy for data set (e.g., many patches from many virus sequences) diversity and/or an ability to rapidly evolve can be considered. In particular, the total energy typically increases for each patch from the data set that does not have a corresponding patch in the epitome that gives a low priming plus attack energy. Equation 1 provides one example of an energy E(x) that satisfies this requirement.

$$E(x) = \sum_S \min_T (E(T) + E(x_S, e_T)). \qquad \text{Equation 1}$$

An effective vaccine can be obtained by finding an epitome that minimizes this energy. It is to be appreciated that Equation 1 is provided for illustrative purposes and sake of brevity, and does not limit the invention.

Each of the above energies (E(T) and $E(x_S, e_T)$) can be considered an energy associated with a stochastic process at equilibrium, wherein the energy is equal to a negative log-probability of the event or process. A suitable priming probability that can be employed in accordance with the subject invention is defined by Equation 2:

$$p(T) \propto \exp(-E(T)), \qquad \text{Equation 2:}$$

and a suitable attack probability that can be employed in accordance with the subject invention can be defined by Equation 3:

$$p(x_S | e_T) \propto \exp(-E(x_S, e_T)). \qquad \text{Equation 3:}$$

Exponentiating both sides of the above equations for the total energy E(x) renders Equation 4, which is a probability of the data set x in terms of the priming and attack probabilities:

$$p(x) \propto \prod_S \max_T (p(x_S|e_T)p(T)), \quad \text{Equation 4}$$

which illustrates an expression that optimizes the epitome via maximizing the likelihood of independently generating all patches from the data set, wherein patch $x_S$ is generated from epitome patch $e_T$ with probability $p(x_S|e_T)$ and patch $e_T$ is selected from the epitome with probability p(T).

In instances where $\Delta E(x_S, e_T)$ is relatively high (e.g., except for substantially perfect matches between $x_S$ and $e_T$), the total energy can be closely approximated as const—rE, wherein r is the number of the patches $x_S$ that match their corresponding epitome patch $e_T$ and E is the binding energy for such matches. The foregoing can be derived by letting $\Delta E$ go to infinity uniformly across mismatches. The const term can depend on $\Delta E$ and/or the total number of patches K, and typically does not depend on the fraction of the matched patches. Thus, for a given size of the epitome, the quality of the vaccine can depend only on the percentage of the matched epitopes.

An exemplary functional form that can behave in this manner in the limit involves the letter substitution probability θ. This probability can be uniformly or non-uniformly spread over any or all other possibilities (e.g., other three nucleotides in case of DNA/RNA sequence models or other nineteen amino acids in case of protein models) as illustrated in Equation 5:

$$p(x_S|e_T)=\theta^{|x_S \neq e_T|}(1-\theta)^{|x_S=e_T|}, \quad \text{Equation 5:}$$

wherein | | is the number of elements in the vector argument that are true, for example, $|x_S=e_T|$ is the number of elements on which the two patches disagree. When the variability parameter θ can approach zero, an exact match model, which is a conservative choice for vaccine design as it limits the assumptions on cross-reactivity, can be utilized. The binding energy model corresponding to this distribution is illustrated in Equation 6:

$$E_{x_s,e_T} = -n\log(1-\theta),\ \Delta E_{x_s,e_T} = |x_{ij} \neq e_{T(ij)}|\log\frac{1-\theta}{\theta}. \quad \text{Equation 6}$$

With amino acid epitomes, the substitution parameter θ can be defined so that it decreases the probability of non-conservative amino acid exchange, thus reflecting to some extent the current understanding of the T cell cross-reactivity. The θ parameter can also be position-dependent. It is to be appreciated that there are other ways of describing the position-specific variability. For example, a full multinomial distribution over possible letters can be utilized in accordance with the subject invention. Utilizing this approach, the full multinomial distribution over possible letters, such as, for example, θA, θC, θT, θG, wherein θx is the probability of letter x at a given position and θA+θC+θT+θG=1 can be employed.

If the epitome is viewed as a stochastic model, the optimization criterion can be written as a likelihood of attacking all epitopes $x_S$ as illustrated in Equation 7:

$$p(\{x_S\}) = \prod_S \sum_T p(x_S|e_T). \quad \text{Equation 7}$$

Under a conservative assumption, wherein θ is approximated to equal to one, this cost can become equivalent to the epitome's coverage of substantially all virus epitopes. If the cost is defined in terms of the total energy barrier summed over substantially all virus epitopes $x_S$, then the free energy can be defined as illustrated in Equation 8:

$$F = \sum_S \sum_T q(T|S)\log\frac{p(T|S)}{p(x_s|e_T)p(T)}, \quad \text{Equation 8}$$

which combines the binding energies described above via an auxiliary distribution q(T|S) for each data patch S.

Individual patch energies $-\log p(x_S|e_T) - \log p(T)$ can be summed to form an estimate of the total energy barrier to the immunity against all forms of the virus if the mapping variable T is known for each sequence fragment S. However, with some probability any piece of the epitome can be chopped and presented by cellular mechanisms and utilized to prime an appropriate T cell, which could later, as a memory cell, bind to an arbitrary HIV patch $x_S$. Thus, similar segments of the epitome can potentially represent a substantially similar antigen $x_S$. The distribution over the epitome correspondence is expressed through q(T|S). In order to compute the average energy over all mappings, an integration under q as a measure of posterior probability of matching the data epitopes to the appropriate epitome patches can be employed. In addition, if the epitome has multiple patches that represent some data epitope $x_S$, such epitome can be more effective than an epitome that has only one way of providing adaptive immunity to this epitope. Thus, the entropy of the distribution q offsets the binding energy, and the free energy of the epitome sequence can be expressed as above. It is to be appreciated that although the epitome and the viruses can go through substantially similar acts, there is no total symmetry of S and T in Equation 8 when optimizing targeting all likely targets S in the virus instead of optimizing the intersection between epitome and a set of viruses.

The free energy minimum can be equal to the negative log likelihood as illustrated in Equation 9:

$$-\log p(\{x_S\}) = \arg\max_q F. \quad \text{Equation 9}$$

Maximizing the likelihood with respect to the epitome e can be equivalent to minimizing the free energy with respect to the posterior distributions q(T|S) for all S and the epitome e. A suitable assignment in the posterior distribution q can require an exact match (e.g., θ=0).

It is to be appreciated that some epitopes are known, but many are not. By studying the escapes in genes, by using databases of epitopes that are known to be immunogenic for some HLA types, or by studying the MHC/cleavege/transport binding data, the probability p(S) can be associated with each peptide $x_S$ in the data, for example, according to how likely the observed pattern is to be presented on the surface of the infected cell, which is the prerequisite for the T cell immunity. If a peptide is not going to be presented, it needs not be included in the epitome and the free energy is defined as illustrated in Equation 10:

$$F = \sum_S p(S) \sum_T q(T|S) \log \frac{p(T|S)}{p(x_S|e_T)p(T)}. \quad \text{Equation 10}$$

Utilizing a conservative assumption (as discussed above), the vaccine optimization algorithm can be defined by Equation 11:

$$e = \lim_{\theta \to 0} \arg \min_e \min_q F. \quad \text{Equation 11}$$

Figure 3:
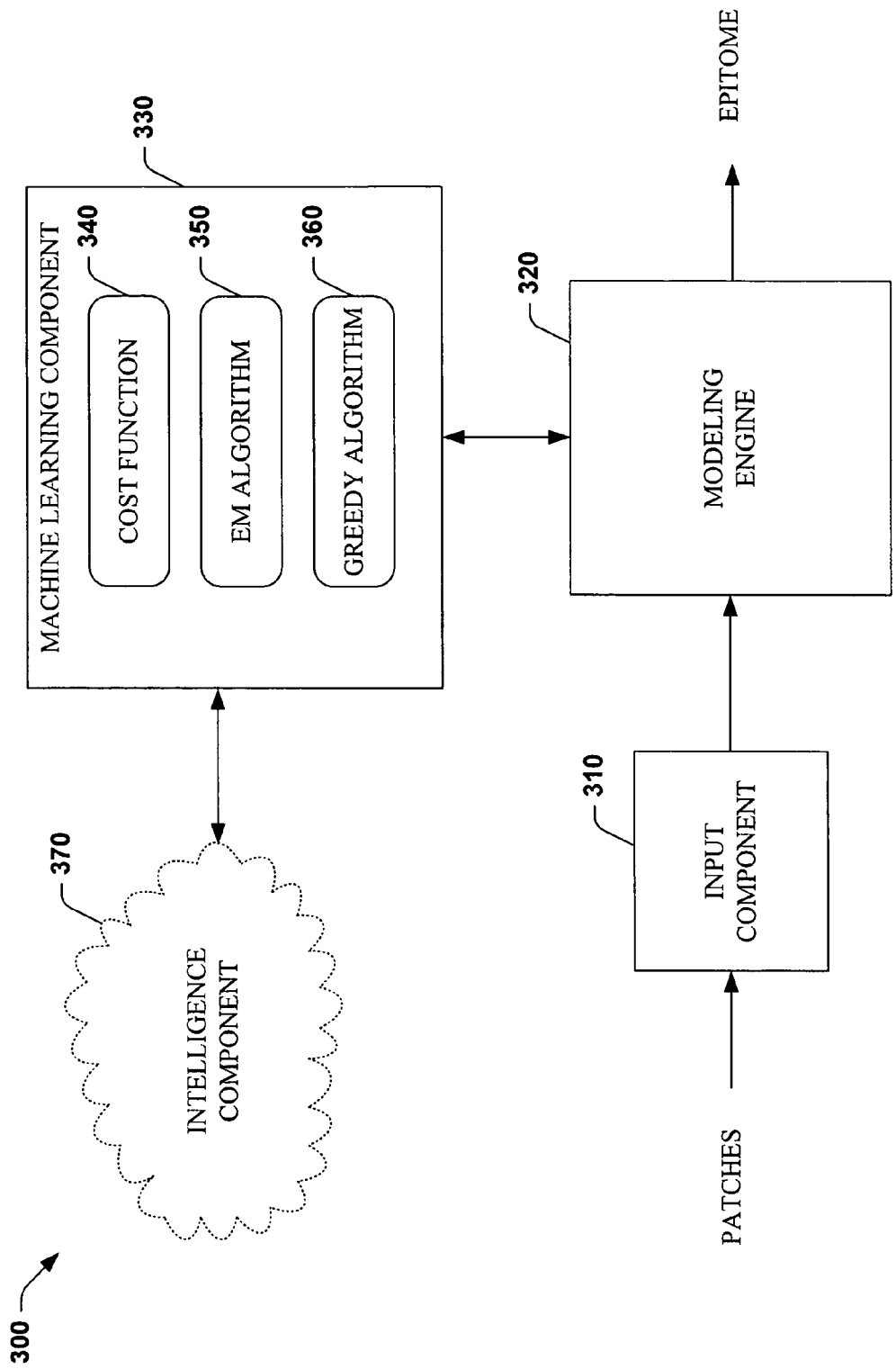

FIG. 3 illustrates a system 300 that determines epitomes via an expectation-maximization (EM) algorithm. The system 300 comprises an input component 310, a modeling engine 320, and a learning component 330. The input component 310 can receive patches and convey them to the modeling engine 320, which can utilize the sequences to determine the epitome. The modeling engine 320 can employ the learning component 330, which can utilize a cost function 340, an EM algorithm 350, and/or a greedy algorithm 360. The modeling engine 320 can employ the EM algorithm 350 to facilitate determining the epitome. For example, by considering the size of the epitome as prescribed (e.g., by vaccine the delivery constraints) and utilizing an initial random guess for the epitome parameters, the above can be performed via an iterative optimization by utilizing the EM algorithm 350.

By way of example, for each $x_S$ the posterior distribution q of positions T can be estimated by Equation 12:

$$q(T|S) = \frac{p(xS|eT)p(T)}{\sum_T p(xS|eT)p(T)}. \quad \text{Equation 12}$$

The epitome that minimizes the free energy can be re-estimated as illustrated in Equation 13 and Equation 14:

$$e_{mn} = \arg\max_{e_{mn}} \sum_{T(i)=(m,n)} q(T|S)[x_{S(i)} = e_{mn}], \quad \text{Equation 13}$$

and $$\theta = \frac{\sum_{m,n} \sum_S p(S) \sum_{T(i)=(m,n)} q(T|S)[x_{S(i)} \neq e_{mn}]}{\sum_{m,n} \sum_S p(S) \sum_{T(i)=(m,n)} q(T|S)}. \quad \text{Equation 14}$$

Iterating these equations is an expectation maximization (EM) algorithm for the epitome model, which reduces the free energy in each act, thus converging to the local minimum of the free energy and the local maximum of the likelihood.

The EM algorithm 350 can jointly and concurrently optimize both the epitome and the binding energy parameters θ. The algorithm can be initialized with a random epitome and a relatively large variability estimate θ. After several iterations, θ generally decreases as the epitome starts to more closely match the data and the uncertainty contracts. The energy barrier $\Delta E_{x_S, e_T}$ to non-exact matches can become relatively steep capturing the conservative assumption on high T cell specificity. If the epitome is not long enough, then the algorithm decreases the allowed variability (and thus increases specificity) to a level where the balance between covering all the data and allowing for as little cross-reactivity as possible is reached for the assumed energy model. The variability can be further decreased to force the model to fit as many patches as possible without any latitude on cross-reactivity. It is to be appreciated that various other algorithms such as the greedy algorithm, Hidden Markov model, neural network, and/or Bayesian-based algorithms can be utilized in accordance with an aspect of the subject invention. For example, the greedy algorithm can be utilized to jointly update the size of the epitome sequence or sequences and the free energy in a greedy fashion.

Optionally, an intelligence component 370 can be employed in accordance with an aspect of the invention. In one instance, the intelligence component 370 can be utilized to facilitate determining which learning algorithm to employ. For example, the machine learning component 360 can provide various cost functions, expectation-maximization algorithms, greedy algorithms, etc. as described above. The intelligence component 370 can determine which algorithm(s) should be employed, for example, based on a desired vaccine, a set of input patches, epitope length, etc. In addition, the intelligence component 370 can perform a utility-based analysis in connection with selecting an algorithm to utilize, with determining an epitome, and/or with optimizing an epitome.

In another aspect of the invention, the intelligent component 370 can perform a probabilistic and/or statistic-based analysis in connection with inferring and/or determining a suitable machine learning algorithm and/or an epitome. As utilized herein, the term "inference" and variations thereof refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines . . . ) can be employed in connection with performing automatic and/or inferred action in connection with the subject invention.

Figure 4:
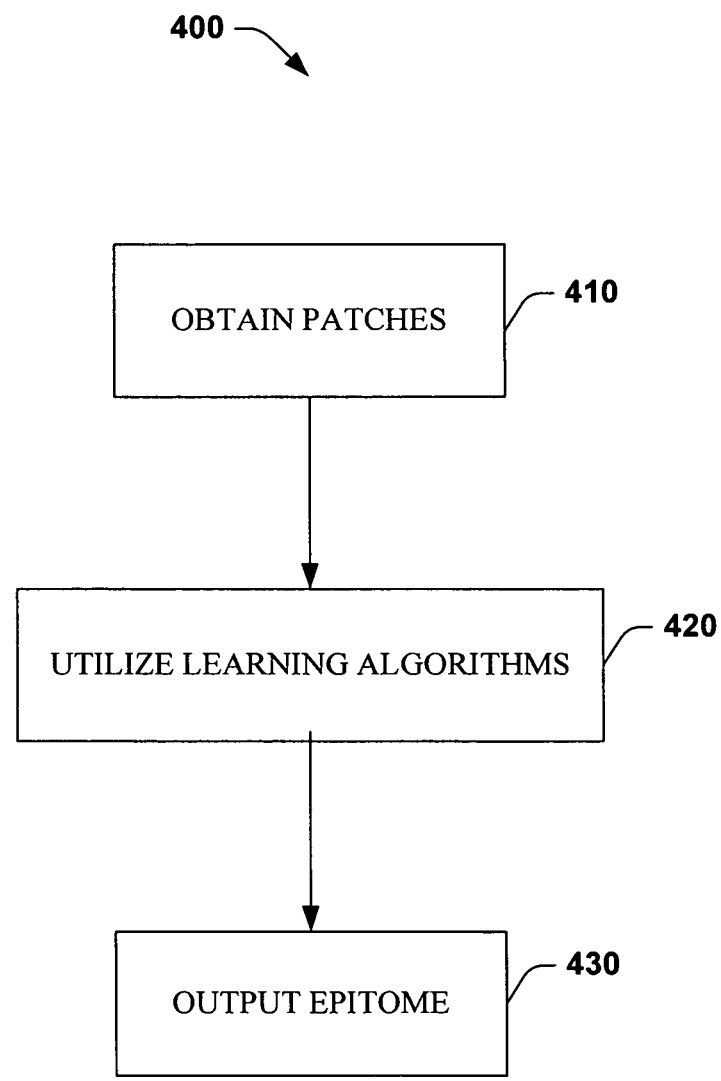
Figure 5:
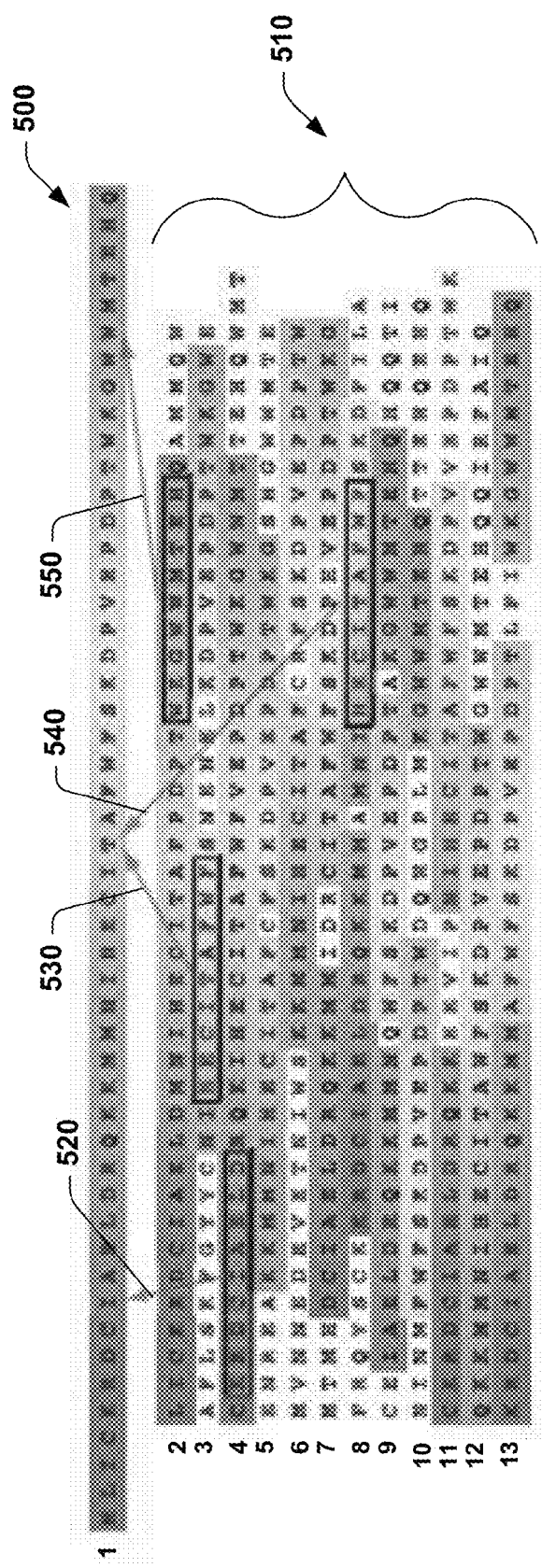
Figure 6:
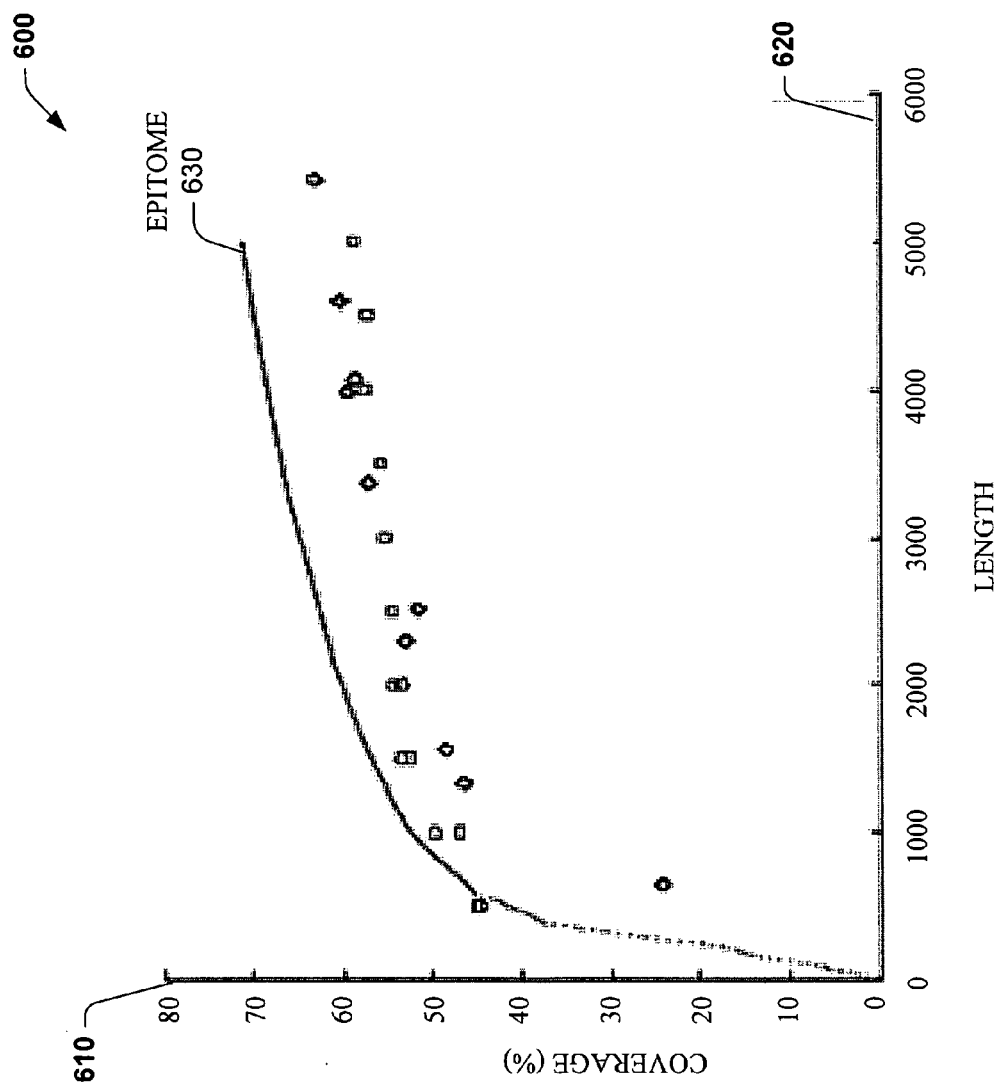
Figure 7:
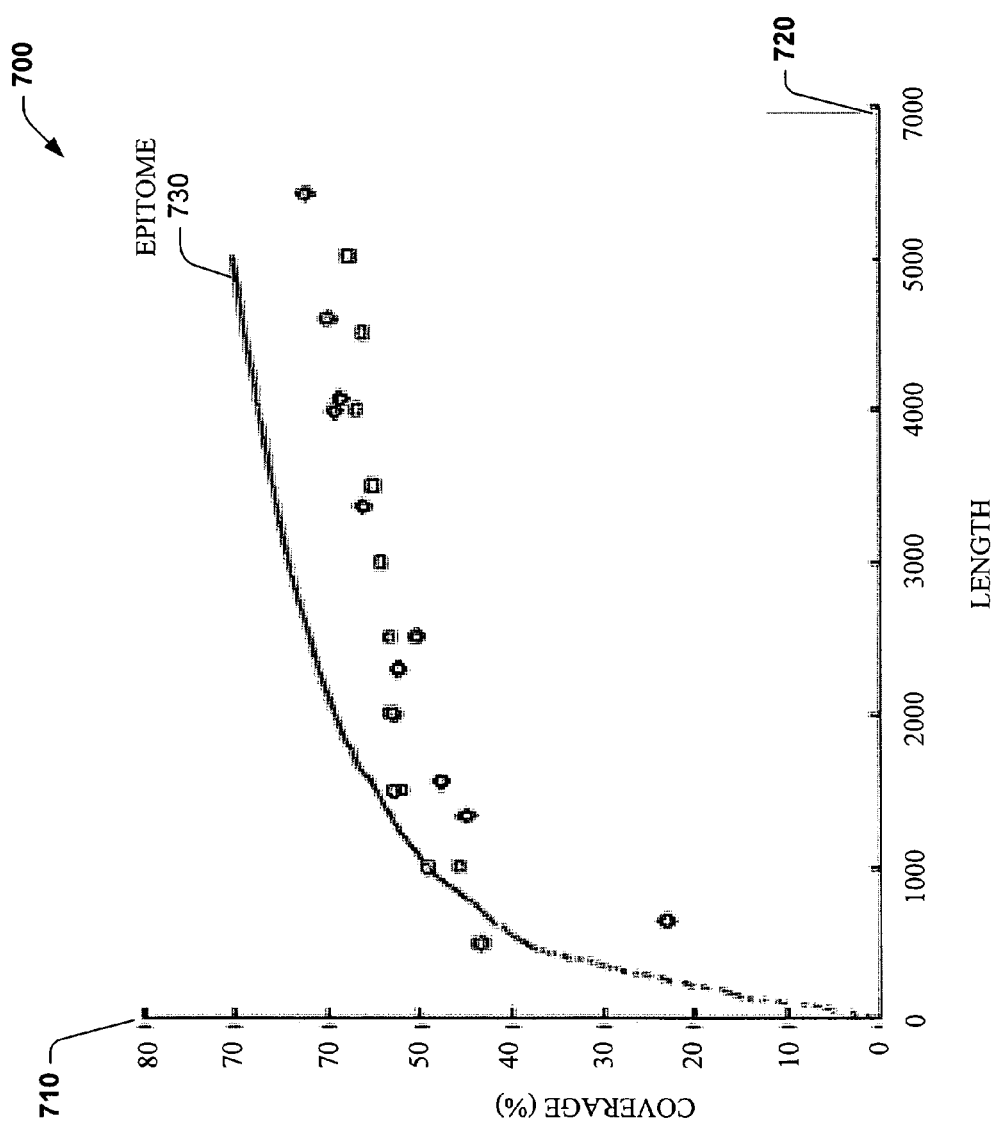

FIG. 4 illustrates a methodology 400 that determines epitomes for pathogens such as HIV. For simplicity of explanation, the methodology is depicted and described as a series of acts. It is to be understood and appreciated that the present invention is not limited by the acts illustrated and/or by the order of acts, for example acts can occur in various orders and/or concurrently, and with other acts not presented and described herein. Furthermore, not all illustrated acts may be required to implement the methodology in accordance with the present invention. In addition, those skilled in the art will understand and appreciate that the methodology could alternatively be represented as a series of interrelated states via a state diagram or events.

At 410, a plurality of patches, or sequences, which can be a subset or all of a population of sequences, is received. Such patches can be variable length, for example, nine-mers, ten-mers, etc. At 420, various learning algorithms can be utilized to determine the epitome, based on the received sequences. For examples, learning algorithms such as a cost function (as described herein), an expectation-maximization (EM) algorithm (as described herein), a greedy algorithm, Bayesian models, Hidden Markov models, neural networks, etc. can be employed in connection with various aspect of the subject invention. It is to be appreciated that the resultant epitome can be a most likely epitome such as an epitome that includes a sequence with the greatest coverage, a shortest sequence for a particular coverage, etc. At reference numeral 430, the epitome can be output. It is to be appreciated that such an epitome can be utilized to create peptide and/or nucleotide sequencing to generate an AIDS vaccine cocktail. This novel approach can provide for improvements over traditional techniques by modeling sequence diversity through machine learning. Resulting vaccines (for HIV) can provide for higher epitope coverage in comparison with the cocktails of consensi, phylogenetic tree nodes and random strains from the data.

FIG. 5 illustrates an exemplary epitome 500 and a plurality of patches (sequences) 510 that the epitome 500 epitomizes in terms of linear nine-amino acid epitopes, assuming that all nine-mers are equally immunogenic and exposure to the immune system leads to no cross-reactivity. The identified row numbers and their corresponding SEQ ID NO is provided as follows: Row 1 (SEQ ID NO: 1); Row 2 (SEQ ID NO: 2); Row 3 (SEQ ID NO: 3); Row 4 (SEQ ID NO: 4); Row 5 (SEQ ID NO: 5); Row 6 (SEQ ID NO: 6); Row 7 (SEQ ID NO: 7); Row 8 (SEQ ID NO: 8); Row 9 (SEQ ID NO: 9); Row 10 (SEQ ID NO: 10); Row 11 (SEQ ID NO: 11); Row 12 (SEQ ID NO: 12); and Row 13 (SEQ ID NO: 13). Although nine-mers are depicted, it is to be appreciated that essentially any mer (e.g., ten-mers, eleven-mers, etc.) can be utilized in various aspects of the subject invention, and any or all assumptions can be relaxed. As illustrated at 520, 530, 540 and 550, three portions of the epitome 500 can be matched with various portions of the plurality of sequences. Such matching can be achieved by moving a window (e.g., nine-long, as depicted in FIG. 5) over the epitome 500, for example, from left to right. While moving the window, the window can be matched with a corresponding sequence epitopes. The epitome 500 can be estimated from the data by chopping up the input sequences 510 into short peptides of epitope length or longer and creating a mosaic sequence longer than any given data sequence, but much shorter than the sum of all input sequence lengths. It is to be appreciated that even though it may be desirable to achieve coverage of short epitopes, due to the overlaps in these epitopes in the data, the epitome may favor conservation of long amino acid stretches from the epitomized sequences. Therefore, the epitome can also be viewed as a collection of longer or shorter protein pieces needed to compose each of the given sequences.

FIG. 6 depicts a graph 600 that illustrates epitome coverage of a plurality of different CAG genes over length, and FIG. 7 depicts a graph 700 that illustrates epitome coverage of various epitopes of a GAG gene over length. In these figures, respective axes 610 and 710 correspond to coverage as a function of percent and respective axes 620 and 720 corresponds to length. In this example, epitomes of size 1×Ne can be utilized. However, as a vaccine the epitome may need to be delivered in a different format, which can be achieved by chopping the 1×Ne epitome into smaller pieces or directly optimizing an epitome of a required format as described herein. The patches derived from the sequence data can include all possible contiguous amino acid subsequences, for example, of size nine, corresponding to the length of a typical epitope, with indices S=11, 12, . . . , 19. In order to include a context that can affect escape, the patches may need to be longer. However, optimizing for coverage of shorter patches can lead to preservation of a larger context around any or all patches due to patch overlaps both in data and in the epitome. To compute various vaccine components, an expectation-maximization (EM) algorithm, a greedy algorithm, and the like can be utilized to train a mixture of profile sequences, for example, sequences in which each site has an associated most likely letter and a probability of generating any other letter.

Epitomes of various sizes can be utilized, wherein such epitomes can be constructed by iteratively increasing the size of the epitome and decreasing the free energy with the assumption $\theta=0$, thus increasing coverage of the epitopes from the data. Respective acts can be optimal incremental moves, for example, by adding a most frequent data patch that is not yet included in the epitome. This optimization follows a conservative assumption that none of the epitopes in the sampled viruses should be a priori ignored in an effective vaccine (e.g., p(S)=const) and only an exact copy of epitope in the vaccine will lead to an effective vaccine ($\theta=0$). Thus, the efficiency of the optimization algorithms can be evaluated by a percentage of the data patches that are exactly copied in the epitome. As discussed previously, coverage is related to the free energy and can be more intuitive when $\theta=0$.

In order to provide additional context for implementing various aspects of the present invention, FIG. 8 and the following discussion is intended to provide a brief, general description of a suitable computing environment in which the various aspects of the present invention may be implemented. While the invention has been described above in the general context of computer-executable instructions of a computer program that runs on a local computer and/or remote computer, those skilled in the art will recognize that the invention also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multiprocessor computer systems, minicomputers, mainframe computers, as well as personal computers, hand-held computing devices, microprocessor-based and/or programmable consumer electronics, and the like, each of which may operatively communicate with one or more associated devices. The illustrated aspects of the invention may also be practiced in distributed computing environments where certain tasks are performed by remote processing devices that are linked through a communications network. However, some, if not all, aspects of the invention may be practiced on stand-alone computers. In a distributed computing environment, program modules may be located in local and/or remote memory storage devices.

With reference to FIG. 8, an exemplary environment 800 for implementing various aspects of the invention includes a computer 812. The computer 812 includes a processing unit 814, a system memory 816, and a system bus 818. The system bus 818 couples system components including, but not limited to, the system memory 816 to the processing unit 814. The processing unit 814 can be any of various available processors. Dual microprocessors and other multiprocessor architectures also can be employed as the processing unit 814.

The system bus 818 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), and Small Computer Systems Interface (SCSI).

The system memory 816 includes volatile memory 820 and nonvolatile memory 822. The basic input/output system (BIOS), containing the basic routines to transfer information between elements within the computer 812, such as during start-up, is stored in nonvolatile memory 822. By way of illustration, and not limitation, nonvolatile memory 822 can include read only memory (ROM), programmable ROM (PROM), electrically programmable ROM (EPROM), electrically erasable ROM (EEPROM), or flash memory. Volatile memory 820 includes random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

Figure 8:
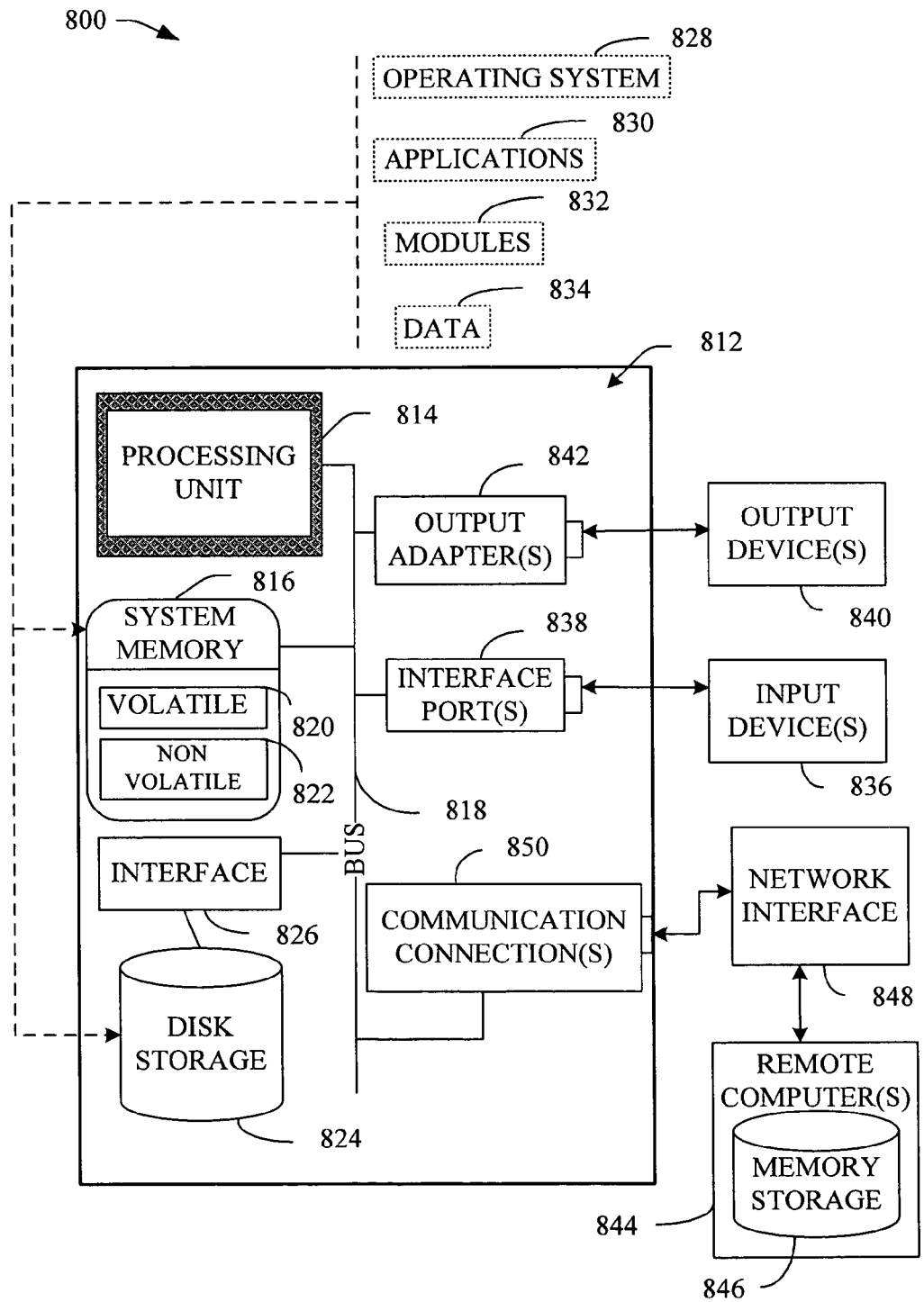

Computer 812 also includes removable/non-removable, volatile/non-volatile computer storage media. FIG. 8 illustrates, for example a disk storage 824. Disk storage 824 includes, but is not limited to, devices like a magnetic disk drive, floppy disk drive, tape drive, Jazz drive, Zip drive, LS-100 drive, flash memory card, or memory stick. In addition, disk storage 824 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 824 to the system bus 818, a removable or non-removable interface is typically used such as interface 826.

It is to be appreciated that FIG. 8 describes software that acts as an intermediary between users and the basic computer resources described in the suitable operating environment 800. Such software includes an operating system 828. Operating system 828, which can be stored on disk storage 824, acts to control and allocate resources of the computer system 812. System applications 830 take advantage of the management of resources by operating system 828 through program modules 832 and program data 834 stored either in system memory 816 or on disk storage 824. It is to be appreciated that the present invention can be implemented with various operating systems or combinations of operating systems.

A user enters commands or information into the computer 812 through input device(s) 836. Input devices 836 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 814 through the system bus 818 via interface port(s) 838. Interface port(s) 838 include, for example, a serial port, a parallel port, a game port, and a universal serial bus (USB). Output device(s) 840 use some of the same type of ports as input device(s) 836. Thus, for example, a USB port may be used to provide input to computer 812, and to output information from computer 812 to an output device 840. Output adapter 842 is provided to illustrate that there are some output devices 840 like monitors, speakers, and printers, among other output devices 840, which require special adapters. The output adapters 842 include, by way of illustration and not limitation, video and sound cards that provide a means of connection between the output device 840 and the system bus 818. It should be noted that other devices and/or systems of devices provide both input and output capabilities such as remote computer(s) 844.

Computer 812 can operate in a networked environment using logical connections to one or more remote computers, such as remote computer(s) 844. The remote computer(s) 844 can be a personal computer, a server, a router, a network PC, a workstation, a microprocessor based appliance, a peer device or other common network node and the like, and typically includes many or all of the elements described relative to computer 812. For purposes of brevity, only a memory storage device 846 is illustrated with remote computer(s) 844. Remote computer(s) 844 is logically connected to computer 812 through a network interface 848 and then physically connected via communication connection 850. Network interface 848 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 850 refers to the hardware/software employed to connect the network interface 848 to the bus 818. While communication connection 850 is shown for illustrative clarity inside computer 812, it can also be external to computer 812. The hardware/software necessary for connection to the network interface 848 includes, for exemplary purposes only, internal and external technologies such as, modems including regular telephone grade modems, cable modems and DSL modems, ISDN adapters, and Ethernet cards.

As utilized in this application, terms "component," "system," "engine," and the like are intended to refer to a computer-related entity, either hardware, software (e.g., in execution), and/or firmware. For example, a component can be a process running on a processor, a processor, an object, an executable, a program, and/or a computer. By way of illustration, both an application running on a server and the server can be a component. One or more components can reside within a process and a component can be localized on one computer and/or distributed between two or more computers.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the invention. In this regard, it will also be recognized that the invention includes a system as well as a computer-readable medium having computer-executable instructions for performing the acts and/or events of the various methods of the invention.

In addition, while a particular feature of the invention may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. A system that facilitates determining an epitome that provides a basis for a vaccine cocktail, comprising:
   a processing unit;
   a system memory coupled to the processing unit;
   an input component that receives a plurality of overlapping patches $x_S$ corresponding to a set of subsequences from one or more pathogen sequences in a population; and
   a modeling engine that employs one or more machine learning algorithms to determine an epitome based on the plurality of overlapping patches $x_S$, the epitome providing the basis for the vaccine cocktail, wherein the one or more machine learning algorithms comprises an expectation-maximization (EM) algorithm that includes an initial random guess for the epitome and iteratively reduces a free energy of the epitome converging to a local minimum of free energy, wherein the free energy combines T cell binding energy and HLA binding via a variational mapping distribution of respective ones of the plurality of overlapping patches $x_S$ to the epitome.

2. The system of claim 1, wherein the plurality of overlapping patches are pathogen subsequences assembled to generate representative sequences of a category.

3. The system of claim 2, wherein the category comprises at least one of sequences associated with a specific species, sequences associated with a specific clade, sequences associated with an acute phase of infection, or sequences associated with a chronic phase of infection.

4. The system of claim 2, wherein the category comprises HIV.

5. The system of claim 1, wherein at least one of the pathogen subsequences relates to an epitope.

6. The system of claim 1, wherein at least one of the pathogen subsequences comprises an epitope.

7. The system of claim 1, wherein the plurality of overlapping patches comprise short subsequences, at least one of which contains an unknown epitope having a non-zero probability of being presented on a surface of an infected cell.

8. The system of claim 1, wherein at least one of the one or more machine learning algorithms determines an epitome that minimizes an energy needed to mount an effective immune response as determined by a cost function.

9. The system of claim 8, wherein the cost function determines a minimum total energy for a given length of the epitome.

10. The system of claim 1, wherein at least one of the one or more machine learning algorithms minimizes the length of the epitome, the minimization subject to the constraint that the resulting epitome has a cost less than or equal to a given cost.

11. The system of claim 9, wherein the total energy is based at least in part on the free energy.

12. The system of claim 1, wherein the free energy is calculated according to at least one of:
   a frequency of occurrence of one of the plurality of overlapping patches $x_S$ in the population;
   a probability that one of the plurality of overlapping patches $x_S$ is found in a single strain of the population;
   a probability of occurrence of one of the plurality of overlapping patches $x_S$ in a population wherein the sequencing data is ambiguous;
   a value that reflects both the frequency of one of the plurality of overlapping patches $x_S$ and whether one of the plurality of overlapping patches $x_S$ contains a known epitope;
   a probability that one of the plurality of overlapping patches $x_S$ is an epitope;
   a probability that one of the plurality of overlapping patches $x_S$ will be presented by a cell; or a probability that an individual vaccinated with one of the plurality of overlapping patches $x_S$ will mount an immune response.

13. The system of claim 11, wherein the free energy is calculated according to at least one of:
   a frequency of occurrence of one of the plurality of overlapping patches $x_S$ in the population;
   a probability that one of the plurality of overlapping patches $x_S$ is found in a single strain of the population;
   a probability of occurrence of one of the plurality of overlapping patches $x_S$ in a population wherein the sequencing data is ambiguous;
   a value that reflects both the frequency of one of the plurality of overlapping patches $x_S$ and whether one of the plurality of overlapping patches $x_S$ contains a known epitope;
   a probability that one of the plurality of overlapping patches $x_S$ is an epitope;
   a probability that one of the plurality of overlapping patches $x_S$ will be presented by a cell; or
   a probability that an individual vaccinated with one of the plurality of overlapping patches $x_S$ will mount an immune response.

14. The system of claim 8, wherein the cost function measures an inverse similarity of the plurality of overlapping patches with an estimate of the epitope.

15. The system of claim 9, wherein the cost function measures an inverse similarity of the plurality of overlapping patches with an estimate of the epitope.

16. The system of claim 10, wherein the cost function measures an inverse similarity of the plurality of overlapping patches with an estimate of the epitope.

17. The system of claim 8, wherein the cost function is determined according to a hamming distance of less than a fixed integer.

18. The system of claim 8, wherein the cost function is determined according to a probability of one of the plurality of overlapping patches $x_S$ given a patch $e_T$ of the epitope.

19. The system of claim 8, wherein the cost function is determined according to a probability density function of one of the plurality of overlapping patches $x_S$ given a patch $e_T$ of the epitope.

20. The system of claim 8, wherein the cost function comprises an expected fraction of the plurality of overlapping patches relating to one or more strains of the population and wherein expectation is taken over the probability that a patch contains an epitope.

21. The system of claim 9, wherein the cost function comprises an expected fraction of the plurality of overlapping patches relating to one or more strains of the population and wherein expectation is taken over the probability that a patch contains an epitope.

22. The system of claim 8, wherein the cost function between one of the plurality of overlapping patches $x_S$ and a patch $e_T$ of the epitope is an exponential of a binding energy reflecting the binding of a T-cell primed with one peptide to another peptide.

23. The system of claim 1, the plurality of overlapping patches comprising variable length peptides.

24. The system of claim 1, further comprising an intelligence component to optimize the epitope based on inferences.

25. The system of claim 1, wherein the one or more machine learning algorithms model sequence diversity for the pathogen sequences in the population.

26. The system of claim 1, wherein the epitope is an AIDS vaccine cocktail.

27. The system of claim 1, wherein the one or more machine learning algorithms optimize the epitope by maximizing a number of short subsequences that are present in the plurality of overlapping patches.

28. The system of claim 1, wherein the pathogen sequences are peptides and a length of at least one patch is about 8-11 amino acids.

29. The system of claim 1, wherein the free energy is a negative log-probability of an event.

30. Computer-executable instructions for performing a computer-implemented method to determine an epitome to facilitate vaccine design, the computer-executable instructions stored on computer-readable media, the computer-implemented method comprising:
   receiving a plurality of patches to one or more learning algorithms;
   determining an epitome based on the plurality of patches by employing an expectation-maximization (EM) algorithm that includes an initial sequence for the epitome and iteratively reduces a free energy of the epitome converging to a local minimum of free energy, wherein the free energy combines T cell binding energy and HLA binding via a variational mapping distribution of respective ones of the plurality of patches to the epitome;
   matching a portion of the epitome to at least one region of at least one patch by moving a window over the epitome and matching the portion of the epitome included in the window to the at least one region of the at least one patch; and
   utilizing the epitome to design a vaccine.

31. The method of claim 30, wherein the vaccine is an AIDS vaccine.

32. The method of claim 30, further comprising parsing at least one of the patches into shorter sequences of epitope length and creating a mosaic sequence that is longer than any of the shorter sequences.

33. The method of claim 30, wherein the epitome is a mosaic sequence with a length greater than a length of any individual patch, but less than a sum of all patch lengths.

34. The method of claim 30, wherein the EM algorithm is initialized with a large variability estimate for binding energy parameters relative to the binding energy parameters after several iterations of the EM algorithm.

35. The method of claim 30, further comprising packing patches of a defined length into the epitome.

36. The method of claim 31, wherein the epitome is an HIV vaccine cocktail.

37. The method of claim 30, further comprising optimizing the epitome by maximizing a number of short subsequences that are present in the plurality of patches.

38. A system that facilitates identifying an epitome for generating AIDS vaccine cocktails, comprising:
   a processing unit;
   a system memory coupled to the processing unit;
   an input component configured to receive a plurality of overlapping patches having sequences and store at least a subset of the plurality of overlapping patches in the system memory; and
   a machine learning component configured to employ machine learning to model sequence diversity for identifying an epitome to facilitate AIDS vaccine cocktail assembly, wherein the machine learning component comprises:
      a cost function that accounts for acts that are needed to mount an effective immune response; and
      an expectation-maximization (EM) algorithm that includes an initial random guess for the epitome and iteratively reduces a free energy of the epitome converging to a local minimum of free energy, wherein the free energy combines T cell binding energy and HLA binding via a variational mapping distribution of respective ones of the plurality of overlapping patches to the epitome.

39. The system of claim 38, wherein the EM algorithm is initialized with a large variability estimate for binding energy parameters relative to the binding energy parameters after several iterations of the EM algorithm.

40. The system of claim 38, wherein the cost function is determined according to a hamming distance of less than a fixed integer.

41. The system of claim 38, wherein the free energy is calculated according to at least one of:
   a frequency of occurrence of one of the plurality of overlapping patches in the population;
   a probability that one of the plurality of overlapping patches is found in a single strain of the population;
   a probability of occurrence of one of the plurality of overlapping patches in a population wherein the sequencing data is ambiguous;
   a value that reflects both the frequency of one of the plurality of overlapping patches and whether one of the plurality of overlapping patches contains a known epitope;
   a probability that one of the plurality of overlapping patches is an epitope;
   a probability that one of the plurality of overlapping patches will be presented by a cell; or
   a probability that an individual vaccinated with one of the plurality of overlapping patches will mount an immune response.

42. The system of claim 9, wherein the cost function measures an inverse similarity of the plurality of overlapping patches $x_S$ with an estimate of the epitome.

43. The method of claim 30, wherein the free energy is calculated according to at least one of:
   a frequency of occurrence of a patch in the population;
   a probability that patch is found in a single strain of the population;
   a probability of occurrence of patch in a population wherein the sequencing data is ambiguous;
   a value that reflects both the frequency of patch and whether patch contains a known epitope;
   a probability that patch is an epitope;
   a probability that patch will be presented by a cell; or
   a probability that an individual vaccinated with patch will mount an immune response.

44. The system of claim 1, wherein the free energy is calculated according to:
   a frequency of occurrence of one of the plurality of overlapping patches $x_S$ in the population;
   a probability that one of the plurality of overlapping patches $x_S$ is found in a single strain of the population;
   a probability of occurrence of one of the plurality of patches $x_S$ in a population wherein the sequencing data is ambiguous;
   a value that reflects both the frequency of one of the plurality of overlapping patches $x_S$ and whether one of the plurality of patches $x_S$ contains a known epitope;
   a probability that one of the plurality of overlapping patches $x_S$ is an epitope;
   a probability that one of the plurality of overlapping patches $x_S$ will be presented by a cell; and
   a probability that an individual vaccinated with one of the plurality of overlapping patches $x_S$ will mount an immune response.

45. The system of claim 11, wherein the free energy is calculated according to:
   a frequency of occurrence of one of the plurality of overlapping patches $x_S$ in the population;
   a probability that one of the plurality of overlapping patches $x_S$ is found in a single strain of the population;
   a probability of occurrence of one of the plurality of overlapping patches $x_S$ in a population wherein the sequencing data is ambiguous;
   a value that reflects both the frequency of one of the plurality of overlapping patches $x_S$ and whether one of the plurality of overlapping patches $x_S$ contains a known epitope;
   a probability that one of the plurality of overlapping patches $x_S$ is an epitope;
   a probability that one of the plurality of overlapping patches $x_S$ will be presented by a cell; and
   a probability that an individual vaccinated with one of the plurality of overlapping patches $x_S$ will mount an immune response.

46. The method of claim 30, wherein the free energy is calculated according to:
   a frequency of occurrence of a patch in the population;
   a probability that patch is found in a single strain of the population;
   a probability of occurrence of patch in a population wherein the sequencing data is ambiguous;
   a value that reflects both the frequency of patch and whether patch contains a known epitope;
   a probability that patch is an epitope;
   a probability that patch will be presented by a cell; and
   a probability that an individual vaccinated with patch will mount an immune response.

47. The system of claim 1, wherein the free energy F is defined as:

$$F = \sum_S \sum_T q(T|S) \log \frac{q(T|S)}{p(x_s|e_T)p(T)}$$

where S is a sequence fragment, T is a hidden set of vaccine cocktail indices, $e_T$ is a patch in the vaccine cocktail, and q(T|S) is the variational mapping distribution.

* * * * *